Figure 1:
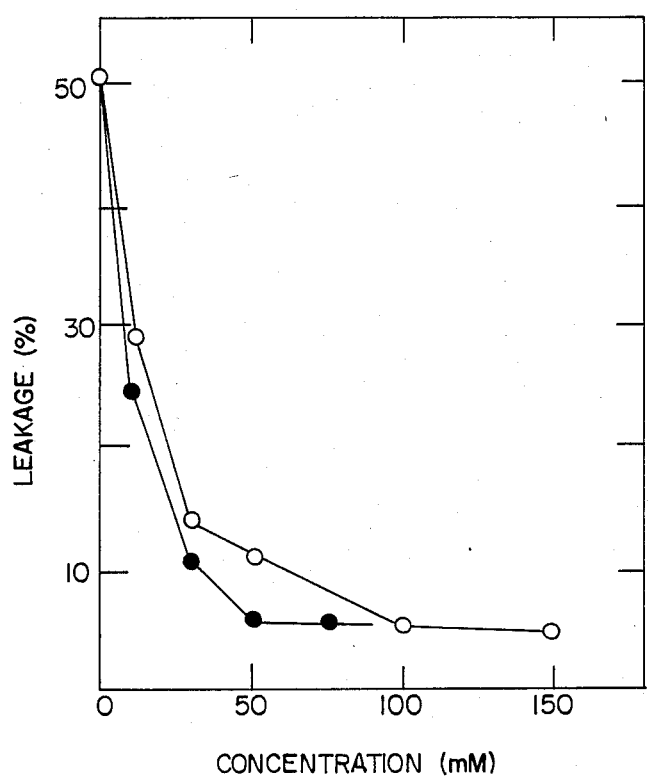

United States Patent [19]

Miyazima et al.

[11] Patent Number: 4,883,665
[45] Date of Patent: Nov. 28, 1989

[54] PROCESS FOR PRODUCING LIPOSOME COMPOSITION

[75] Inventors: Koichiro Miyazima, Uji; Keiko Tomita, Nara; Masayuki Nakagaki, Kyoto, all of Japan

[73] Assignee: Takeda Chemical Industries, Ltd., Osaka, Japan

[21] Appl. No.: 232,539

[22] Filed: Aug. 15, 1988

Related U.S. Application Data

[63] Continuation of Ser. No. 786,305, Oct. 10, 1985, abandoned.

[30] Foreign Application Priority Data

Apr. 11, 1985 [JP] Japan ............................ 60-78173

[51] Int. Cl.$^4$ .................... A61K 37/22; A01N 25/26
[52] U.S. Cl. .................... 424/417; 424/450; 264/4.1; 264/4.3; 264/4.6; 428/402.2
[58] Field of Search ............... 424/417, 450; 428/402.2; 264/4.1, 4.3, 4.6

[56] References Cited

U.S. PATENT DOCUMENTS 4,411,894 10/1983 Schrank et al. .................... 514/22.1

OTHER PUBLICATIONS

Chemical Abstracts 102: 209232w (1984).
Chemical Abstracts 103: 200758K (1985):
Chemical Abstracts 102: 209232w (1984).

*Primary Examiner*—Stanley J. Friedman
*Attorney, Agent, or Firm*—Wenderoth, Lind & Ponack

[57] ABSTRACT

Liposome composition is prepared by freezing liposomes in which a hydrophilic drug and one or more members selected from the group consisting of glucose, galactose, mannose, maltose and maltotriose are entrapped, in the presence of the aqueous solution of one or more members selected from the group of said saccharides. Thus obtained composition can be stably stored under freezing condition, and at thawing treatment, the leakage amount of the hydrophilic agent is exceedingly small.

7 Claims, 2 Drawing Sheets

PROCESS FOR PRODUCING LIPOSOME COMPOSITION

This application is a continuation of now abandoned application Ser. No. 786,305, filed Oct. 10, 1985, now abandoned.

The present invention relates to a process for producing a liposome composition stable to freezing and thawing.

Liposomes can entrap a wide variety of substances including drugs in their internal aqueous space and phopholipid bimolecular layers so that they are expected to be applied in the medical/pharmacology fields as drug carriers for the selective distribution, release control and absorption promotion of the drugs.

It is difficult to keep liposomes as drug carriers stable at room temperature. To solve the problem, cool storage, freeze storage, lyophilization, etc., have been tried. Among them, freeze storage is relatively easy to do, being an effective method of the protection of liposomes from physicochemical changes. However, this has a problem: when liposomes with an entrapped drug are frozen and then thawed at room temperature in their use, some changes are caused in their phospholipid molecular layer structure to accelerate the leakage of the drug. Such leakage is considerable, particularly in the case of hydrophilic drugs.

The inventors, after studying liposomal layer stabilization against freezing and thawing and preventive methods of leakage of entrapped drugs, found that liposomal drugs frozen in the presence of the aqueous solution of a kind of saccharide fulfill the said requirements, and completed this invention after further studies.

That is, the present invention is a process for producing stable liposome compositions, characterized in that liposomes entrapping a hydrophilic drug and one or more members selected from the group consisting of glucose, galactose, mannose, maltose and maltotriose therein are frozen in the presence of the aqueous solution of one or more members selected from the group of said saccharides.

Liposomes are vesicles mainly composed of phospholipid with a bimolecular layer sturcture. In this invention, they are used in the form of multilamellar liposomes in which aqueous spaces surrounded by a single phospholipid bimolecular layer and phospholipid bimolecular layers alternate with each other via the aqueous compartments. For the formation of liposomes; phosphatidyl choline, phosphatidyl ethanolamine, phosphatidyl-inositol, phosphatidyl serine, and sphingomyelin, all of which are obtained from plants or animals such as yolk and soybean, and dimyristyl lecithin, dipalmitoyl lecithin, distearoyl lecithin, all of which are synthetically obtained, can be used as a phospholipid.

As for hydrophilic drugs to be incorporated in liposomes; antitumor agents (adriamycin, actinomycin, mitomycin, 1-$\beta$-arabinofuranosyl cytosine, bleomycin, cisplatin, etc.), antiviral agents (interferon etc.), amino glucosides (gentamicin etc.), antibiotics of $\beta$-lactam and other types (sulbenicillin, cefotiam, cefmenoxime, etc.), peptide hormones (TRH, leuprolide, insulin, etc.), immunopotentiating agents (muramyldipeptide, muramyltripeptide, etc.), and proteins (immunoglobulin, toxins, etc.), are listed.

The ordinary lipsome formation method can be used to entrap a saccharide and a hydrophilic drug in liposomes.

For example:

Phospholipid is dissolved in an organic solvent (e.g., chloroform), the solvent being evaporated to form phospholipid layers. In the dissolution, the coexistence of substances providing charge for phospholipid such as dicetylphosphoric acid and stearylamine is permitted. The aqueous solution of a saccharide and a hydrophilic drug is added to the resulting phospholipid layers to form liposomes. In this case, the saccharide concentration is desired to be in the range of approximately 0.1–2.0 M as monosaccharide residues, whereas the concentration of the hydrophilic drug can be properly specified according to its type and object such that a satisfactory drug effect is obtained. For the formation of liposomes, conventional methods (D. W. Deamer, P. S. Uster, "Liposome" ed. by M. J. Ostro, Marcel Dekker Inc., N.Y., Basel, 1983, p. 27) are applicable: the Voltex method, the ultrasonication method, the ethanol injection method, the ether injection method, the reverse evaporation vesicle method (REV method), and the French press extrusion method. These methods, if necessary, can be used in combination with each other. In such a procedure as described above, liposomes entrapping a saccharide and a hydrophilic drug are obtainable. Hereinafter, the aqueous solution containing a saccharide and hydrophilic drug entrapped in liposomes is simply called the "internal aqueous-phase solution". Phospholipid is generally used in an amount of about 2 to 100 parts by weight relative to one part by weight of the hydrophilic drug.

The said liposomes are next frozen in the presence of the aqueous solution containing one or more of the saccharides mentioned above (glucose, galactose, mannose, maltose, and maltotriose) (hereinafter simply called the "External aqueous-phase solution"). In the freezing process, the hydrophilic drug failing to be entrapped in the liposomes may be removed beforehand according to its type and object. Gel filtration etc. can be employed as a removal method. On the other hand, the aqueous solution containing the saccharide failing to be entrapped in the internal aqueous-phase solution can be used in the freezing process as an external aqueous-phase solution. When a drug failing to be entrapped must be removed as stated above, however, another aqueous solution of the saccharide should be prepared as an external aqueous-phase solution because the saccharide is also removed in the process. The saccharide concentration of the external aqueous-phase solution is desired to be almost equal to that of the internal aqueous-phase solution mentioned above. To the internal and external aqueous-phase solutions, if necessary, a pH control agent, an antioxidant, an antiseptic, etc., can be added.

In the present invention; freezing temperature is below approximately $-30°$ C., preferably below approximately $-50°$ C., both natural freezing and forced freezing using a freezing mixture (e.g., dry ice-acetone) or a freezer can be employed as a freezing method. As for freezing rate, although it is not especially limited, a slow rate, i.e., less than approximately 100° C./min., is generally recomended.

In such a procedure as described above, liposome compositions are obtained as objects in this invention. These liposome compositions are stored under freezing conditions. In their use, they are thawed by an ordinary method at room temperature before being administered to the living body according to the therapeutic object of hydrophilic drugs used.

The present invention, using saccharides safe to the human body, provides a liposome composition with a hydrophilic drug kept stable within their internal aqueous space. The liposome composition can be stably stored under freezing conditions for a long period. Even at thawing treatment in their use, in addition, the leakage amount of the hydrophilic drug is exceedingly small. Therefore, liposomes are expected to be efficiently used as practical drug carriers.

Hereinafter, a more concrete description of this invention is given along with experiments and working examples.

Experiment 1

Yolk lecithin (20 mmole) and dicetylphosphoric acid were dissolved in chloroform at a molar ratio of 10:1, the solvent being evaporated to form thin layers of phospholipid. To the resulting layers, 10 mM 3-(N-morpholino)propanesulfonic acid (MOPS)-NaOH buffer solution (pH 7.2) containing calcein ($4 \times 10^{-4}$ M) as a fluorescence marker was added. The resulting solution, after stirred with Voltex, was subjected to ultrasonication at 0° C. for 30 minutes to prepare liposomes. The resulting liposomes were eluted with calcein-free buffer solution mentioned above, calcein not entrapped in the liposomes being separated by gel chromatography using Sephadex G-50. The liposomes eluted, containing 6.4 mmole yolk lecithin, were put into test tubes and kept frozen for specified periods (10 min. to 2.5 hrs.) by immersing the test tubes in dry ice-methanol or an inorganic-salt refrigerant, at −70° C., −16° C. and −8° C. After the liposome compositions were thawed at room temperature, calcein leakages from the internal aqueous compartments of the liposomes and their turbidities were measured by fluorophotometry (excitation: 490 nm; emission: 520 nm) and optical density at 600 nm, respectively.

On the other hand, the evaluation of the stability of the liposomes to freezing and thawing was done by measuring calcein leakages in liposomes containing various additives as shown in Tables 1 and 2 along with calcein in the above method. The freezing of the liposomes was carried out in the presence of the solution containing said additivies.

TABLE 1

| Additive | Te (°C.) | Leakage % >Te | Leakage % <Te | ΔOD 600 nm >Te | ΔOD 600 nm <Te |
|---|---|---|---|---|---|
| NaCl | −21.1 | 2.5 | 15.7 | 0.02 | 0.28 |
| KCl | −10.7 | 2.0 | 15.5 | — | — |
| Urea | −15.0 | 1.0 | 23.0 | 0.02 | 0.19 |
| Mannitol | −2.5 | — | 35.8 | — | 0.34 |
| No additive | — | — | 51.0 | — | 0.70 |

TABLE 2

| Saccharide | Leakage % | ΔOD 600 nm |
|---|---|---|
| D-glucose | 4–7 | 0.01–0.02 |
| D-galctose | 3–4 | 0.01 |
| D-mannose | 4–5 | 0.01 |
| No saccharide | 51.0 | 0.70 |

ΔOD 600 nm: indicating the difference of optical density before and after thawing treatment.

Table 1 shows comparisons in calcein leakages between the cases of various additives and the case of no additive. When NaCl, KCl, urea, or mannitol, was added by 100 mM; relatively high eutectic points (Te) were observed, higher leakages and turbidities being obtained at freezing temperatures below than each Te. By this is meant that changes in phospholipid structures were caused. On the other hand, D-glucose, D-galactose, or D-mannose was added by 100 mM; no Te was observed even at −70° C., calcein leakages being 3–7% at most, turbidities being low as well (see Table 2). This reveals that the liposomal layers were stabilized against freezing and thawing. In this experiment, Te values were measured using a differential scanning calorimeter (DSC-30 type, Shimadzu Corp., Japan).

Experiment 2

In the same manner as shown in Experiment 1, calcein leakages were measured at different concentrations of saccharides added to liposomes containing both calcein and D-glucose or maltose in their internal and external aqueous spaces.

FIG. 1 shows the relationship between saccharide concentration and calcein leakage as of that obtained when liposome composition which was obtained by freezing liposome entrapping both calcein and D-glucose or maltose in the presence of the aqueous solutions of these saccharides were thawed. When more than 100 mM D-glucose or more than 50 mM maltose was added, considerable inhibitory effects on calcein leakage were observed. It was found that the addition of more than 100 mM saccharide as D-glucose has a clear effect on calcein leakage inhibition.

Experiment 3

In the same manner as shown in Experiment 1; liposomes containing both calcein and 30 mM D-glucose, 30 mM maltose, 30 mM maltotriose, 30 mM maltopentose, or 10 mM dextran T10, in their internal and external aqueous-phase solutions, were prepared, and the relationships between the number of monosaccharide residues composing each of the said saccharides and calcein leakage and liposome turbidity were then determined.

Figure 2:
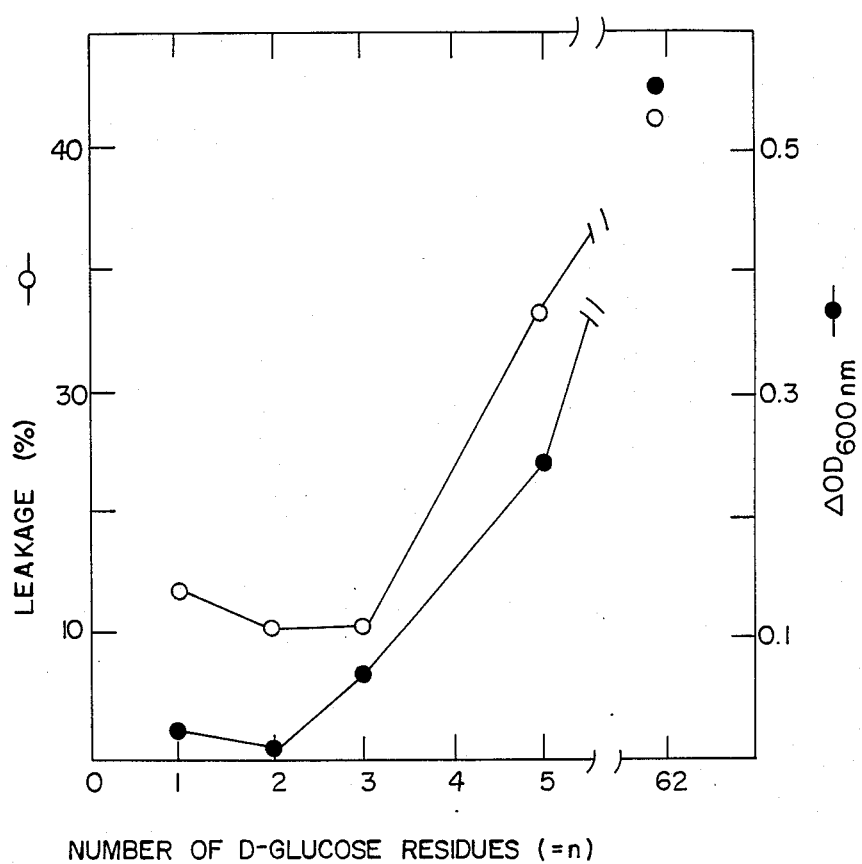

The results obtained are shown in FIG. 2, where n indicates the number of glucose residues (n=1, D-glucose; n=2: maltose; n=3: maltotriose; n=5; maltopentose; and n=62: dextran T10). As revealed in FIG. 2, it was found that the increase in calcein leakage and liposome turbidity due to freezing are efficiently inhibited by the addition of a saccharide with 3 or less monosaccharide residues.

EXAMPLE 1

In place of calcein, 10 mM ara-C (1-β-arabinofuranosyl cytosine) or both 10 mM ara-C and 100 mM D-glucose were added and liposomes were prepared by the same treatments as shown in Experiment 1. The resulting liposomes were put into test tubes and kept frozen for 30 minutes by immersing the test tubes in a refrigerant at −70° C. After the liposomes were thawed at room temperature, ara-C leakages from the liposomes were measured by the absorbance at 196 nm.

| Additive | Leakage |
|---|---|
| D-glucose, 100 mM | 6% |
| No additive | 53% |

EXAMPLE 2

In place of calcein, 10 mM leuprolide both 10 mM leuprolide and 1 M D-galactose were added, and liposomes were prepared by the same treatments as shown in Experiment 1. The resulting liposomes were put into test tubes and kept frozen for 30 minutes by immersing the test tubes in a refrigerant at −70° C. After the liposomes were thawed at room temperature, leuprolide leakages from the liposomes were measured by liquid chromatography at 220 nm absorbance.

| Additive | Leakage |
| --- | --- |
| D-galactose, 1M | 4% |
| No additive | 40% |

What we claim is:

1. A process for producing liposome compositions, which comprises (1) preparing liposomes entrapping an internal aqueous solution composed of (a) an effective amount of a hydrophilic drug selected from the group consisting of antitumor agents, antiviral agents, antibiotics, peptide hormones, enzymes, immunopotentiating agents or proteins and (b) at least one saccharide selected from the group consisting of D-glucose, D-galactose, D-mannose and maltose in a concentration of 0.1 to 1M, wherein the concentration of maltose is based on the molarity converted to glucose units, (2) adding the resulting liposomes to an external aqueous solution containing at least one member selected from the group consisting of glucose, galactose, mannose, maltose in a concentration of 0.1 to 1M, wherein the concentration of maltose is based as above, and (3) freezing the resulting aqueous solution containing the liposomes.

2. The process according to claim 1, wherein the freezing is carried out at a temperature below −30° C.

3. The process according to claim 1, wherein the member is D-glucose.

4. The process according to claim 1, wherein the member is D-galactose.

5. The process according to claim 1, wherein the member is D-mannose.

6. The process according to claim 1, wherein the member is maltose.

7. The process according to claim 1 wherein the saccharide concentration of the external aqueous phase solution is almost equal to that of the internal aqueous phase solution.

* * * * *